United States Patent [19]

Yoshida et al.

[11] Patent Number: 4,892,934

[45] Date of Patent: Jan. 9, 1990

[54] PROCESS FOR PREPARING HYBRIDOMA CELLS WHICH PRODUCE TUMOR-SPECIFIC MONOCLONAL ANTIBODIES

[75] Inventors: Hajime Yoshida; Nobuo Hanai, both of Kanagawa, Japan

[73] Assignee: Kyowa Hakko Kogyo Kabushiki Kaisha, Japan

[21] Appl. No.: 244,601

[22] Filed: Sep. 14, 1988

Related U.S. Application Data

[63] Continuation of Ser. No. 709,967, Mar. 11, 1985, abandoned.

[30] Foreign Application Priority Data

Mar. 12, 1984 [JP] Japan .................. 59-46683

[51] Int. Cl.$^4$ .................. C07K 15/14; A61K 39/395; C12N 15/00
[52] U.S. Cl. .................. 530/387; 435/240.27; 435/70.21; 435/172.2; 424/85.8; 530/806; 530/808; 530/828; 935/105
[58] Field of Search .................. 530/387, 806, 828; 424/85.8, 68, 70; 435/240.27, 172.2; 935/105

[56] References Cited

U.S. PATENT DOCUMENTS 4,427,653  1/1984  Springer .................. 424/85
4,513,088  4/1985  Levy .................. 436/518
4,666,845  5/1987  Mattes .................. 435/240

OTHER PUBLICATIONS

Middleton, S. et al, Fed. Proc. 39:3464 (1980).
Sharpe, R. J. et al, Transplantation Proceedings, 17(6): 2757–2759 (12-1985).
Golumbeski, G. S. et al, Analytical Biochemistry, 154: 373–381 (1986).
Hanai, N. et al, Cancer Research, 46: 4438–4443 (9-1986).
Sharpe, R. J. et al, Med. Hypotheses 17(3): 265–270 (1985), cited in Biosis Abstract 85:407403.
Kohler and Milstein, Nature, 256, pp. 495–497 (1975).

Primary Examiner—Margaret Moskowitz
Assistant Examiner—Jeff Kushan
Attorney, Agent, or Firm—Wolder, Gross & Yavner

[57] ABSTRACT

High-yielding hybridoma cell lines which secrete monoclonal antibodies capable of binding to tumor cells of one or more types, but not normal cells can be obtained more readily by fusing myeloma cells with antibody-forming cells isolated from an animal immunized with tumor antigens, which has previously been made immunological tolerant to normal cell antigens, comprising the total antigens, or at least a proportion of the total antigens, of the normal cells corresponding to the tumor cells chosen as the source of immunizing antigens.

7 Claims, No Drawings

PROCESS FOR PREPARING HYBRIDOMA CELLS WHICH PRODUCE TUMOR-SPECIFIC MONOCLONAL ANTIBODIES

This application is a continuation of application Ser. No. 709,967, filed 3/11/85, now abandoned.

FIELD OF THE INVENTION

The present invention relates to a process for preparing hybridoma cells which produce monoclonal antibodies capable of binding to tumour cells of one or more types, but substantially not to normal cells. Such monoclonal antibodies are hereinafter referred to as tumour-specific monoclonal antibodies.

DESCRIPTION OF THE PRIOR ART

It is particularly desired to obtain monoclonal antibodies specific for antigens which are components of human tumour cells, but not normal human cells. Such monoclonal antibodies may be used for the diagnosis and treatment of appropriate human tumours and for analysis of human tumour antigens.

Previously, antisera have been prepared which are reactive with human tumour cells by immunizing various animals with human tumour antigens of the same cells, generally the total antigens of the tumour cells or the membrane antigens of the same cells. If, however, an animal is immunized with whole tumour cells or membrane fragments of tumour cells, the antiserum which can be obtained from the immunized animal is capable of reacting with normal cells as well as tumour cells, since the majority of the immunizing antigens are common to both tumour cells and normal cells. Tumour-specific antibodies cannot be readily isolated from such an antiserum.

Following the report on the preparation of monoclonal antibody-secreting hybridoma cells by Köhler and Milstein in 1975 [Nature, 256, 495–497 (1975)], many researchers proposed to produce hybridoma cells which secrete tumour-specific monoclonal antibodies by fusing antibody-forming cells derived from animals immunized with tumour antigens and non-immunoglobulin secreting myeloma cells. When such cell fusions are carried out, the vast majority of resulting hybridoma cells secrete monoclonal antibodies which bind to antigen determinants common to both normal and tumour cells and hybridoma cells which secrete tumour-specific monoclonal antibodies must be isolated by careful selection. When tumour-specific monoclonal antibody-producing hybridoma cells have been thus prepared and cloned, the production yields of practically useable clones have often been found to be very low. There is thus a need for a more advantageous process for preparing hybridoma cells which produce tumour-specific monoclonal antibodies.

SUMMARY OF THE INVENTION

We have found that it is possible to obtain more readily high-yielding hybridoma cell lines which secrete tumour-specific monoclonal antibodies by using antibody-forming cells isolated from animals immunized with tumour antigens (e.g. fragments of neoplastic tissue, isolated tumour cells or membrane fragments of tumour cells), which have previously been made immunologically tolerant (or immunologically unresponsive) to normal cell antigens, comprising the total antigens, or at least a proportion of the total antigens, of the normal cells corresponding to the tumour cells chosen as the source of the immunizing antigens. By preparing hybridoma cells in such a manner using human tumour antigens for immunization, we have obtained particularly useful tumour-specific monoclonal antibodies capable of binding to human tumour cells of one or more types.

According to one aspect of the present invention, we therefore provide a process for preparing hybridoma cells which produce a tumour-specific monoclonal antibody by immunizing a suitable animal with tumour antigens, fusing antibody-forming cells isolated from the immunized animal with non-immunoglobulin secreting myeloma cells and selecting hybridoma cells which secrete a desired monoclonal antibody capable of binding to a tumour-specific antigen, characterized in that the animal chosen for immunization is first made immunologically tolerant to normal cell antigens, comprising at least a proportion of the total antigens of the normal cells corresponding to the tumour cells chosen as the source of the immunizing antigens. (The normal cell antigens to which the animal chosen for immunization is made immunologically tolerant are hereinafter collectively referred to as the tolerogen).

Hybridoma cells prepared by a process according to the present invention can be cultured in vitro or administered intraperitoneally to a syngeneic animal (i.e. cultured in vivo) for the purpose of obtaining in good yield the tumour-specific monoclonal antibody synthesized by the cells. The monoclonal antibody is isolated from the culture medium or ascites fluid respectively using conventional methods.

Conveniently, appropriate tumour tissue fragments, appropriate isolated whole tumour cells, an appropriate broken tumour cell preparation or membrane fragments thereof can be used for immunization. Particularly preferred for immunization are tumour antigens originating from human tumours, especially human lung, stomach, large intestine, pancreatic, liver, endometrium, cervical, kidney, bladder and cerebral tumours. The animal chosen for immunization will generally be a mouse or rat.

As the tolerogen, it is preferred to use (a) one member selected from isolated cells, broken cells, tissue fragments and membrane fragments originating from a normal organ of the same type as that from which the tumour antigens chosen for the subsequent immunization are derived, or (b) one member selected from isolated cells, broken cells, tissue fragments and membrane fragments originating from various normal organs comprising appropriate antigens. It is possible for the tolerogen to be one member selected from isolated cells, broken cells, tissue fragments and membrane fragments originating from a normal organ of a different type than the organ from which the tumour antigens used for immunization are derived. If desired, more than one appropriate individual may be used for the preparation of the tolerogen.

Induction of immunological tolerance

Immunological tolerance to an antigen may usually be induced in an adult animal by administration of the antigen in a larger amount than normally used for immunization. Immunological tolerance to certain antigens can also be induced in adult animals by repeated administration of the antigen in a much smaller amount than normally used for immunization. In the case of a newborn animal (e.g. 24 hours after birth), it is generally possible to induce immunological tolerance to an antigen by administration of a dose of the antigen lower than the normal adult immunization dose.

In a hybridoma cell preparation process according to the present invention, the preferred dose of tolerogen depends both on the nature of the tolerogen and the type of animal chosen for treatment with the tolerogen. If a tolerogen of normal cells or membrane fragments of normal cells is employed, and the animal to be treated is a mouse, the preferred dose will generally be as indicated below.

(a) Adult animal—larger dose than usual for immunization: 10–100 ×the usual dose for immunization.
[for example, $5 \times 10^5$–$10^7$ cells, 1–20 mg of membrane fragments]

(b) Adult animal—smaller dose than usual for immunization: 1/10–1/100×the usual dose for immunization
[for example, $10^2$–$5 \times 10^3$ cells, 0.1 ug-10

(c) dose for newborn animal (e.g. 24 hours after birth): more than $10^5$ cells, more than 100 µg of membrane fragments.

More effective and more stable immunological tolerance can be induced in a neonatal animal than an adult animal. In order to prepare a hybridoma cell by a process according to the present invention, it is thus generally preferable to administer the chosen tolerogen in an appropriate amount to a neonatal animal, for example, an animal born 24 hours previously.

Immunization and preparation of antibody-forming cells

Following induction of tolerance to normal cell antigens in the chosen animal, immunization of the same animal (the tolerant animal) with tumour antigens may be effected, for example, by administration of one member selected from tumour tissue fragments, isolated tumour cells, broken tumour cells and membrane fragments of tumour cells, together with a suitable adjuvant for example, Freund's complete adjuvant, aluminium hydroxide gel and pertussis adjuvant. The administration may be effected by subcutaneous, intravenous or abdominal injection.

For immunization, tumour tissue fragments, isolated tumour cells, broken tumour cells and membrane fragments of tumour cells may be prepared as follows.

(a) Tumour tissue fragments

A suitable tissue, either immediately after dissection or after freezing and defrosting, is cut into small pieces (e.g. 1–2 mm×1–2 mm). The small fragments are implanted under the skin of the animal.

(b) Isolated tumour cells

A suitable tissue is cut into small pieces and homogenized. The homogenized cells are suspended in a suitable solution, for example, a PBS solution, and the cell suspension is administered to the animal chosen for immunization by, for example, subcutaneous or intraperitoneal injection (suitable immunization dose for mice: $10^6$–$10^7$ cells).

(c) Broken cell preparation

Suitable cells are crushed or ground and administered to the animal chosen for immunization by, for example, subcutaneous or intraperitoneal injection.

(d) Membrane fragment preparation

A suitable broken cell preparation is centrifuged at 10,000 g and the resulting supernatent is further centrifuged at 100,000 g. The precipitated fraction is suspended in a suitable solution, for example, a PBS solution and the resulting suspension (the membrane fragment preparation) is administered to the animal chosen for immunization by, for example, subcutaneous or intraperitoneal injection. (Suitable immunization dose for mice: 10–500 µg, calculated as protein).

After the primary immunization, the chosen tumour antigens may be administered 2–5 times with an interval of 1–2 weeks. In the case of a newborn tolerant animal, immunization is preferably carried out at 3–10 weeks after birth, for example, 8 weeks after birth. 3–7 days after every immunization, blood may be collected from the orbital plexus vein and the reactivity of the antiserum to various isolated normal cells, normal tissues, isolated tumour cells, tumour tissues and membrane fragment preparations derived from normal and tumour cells investigated by an enzyme-linked immunosorbent assay method. A suitable enzyme-linked immunosorbent assay method is hereinafter described [see also "Koso Meneki Sokuteiho", published by Igaku Shoin, 1976].

Enzyme-linked immunosorbent assay (a) With a membrane fragment preparation

A membrane fragment preparation of normal or tumour cells (containing 10–1000 µg/ml protein) is into wells of an ELISA plate with 96 wells (Flow Laboratories, U.S.A.) such that the amount per well is 100–200 µl. The plate is allowed to stand at 4° C. over 1–2 nights, and bovine serum albumin (BSA) is coated on the bottom surface of each well. After removal of the supernatant, each well is well-washed with deionized water or a PBS solution (disodium phosphate 1.83g; monopotassium phosphate 0.2lg; sodium chloride 7.65 g; deionized water 1 l; pH 7.2). Then, 100–200 µl of a 1% BSA-PBS solution is added to each well and the plate is allowed to stand at 4° C. over 1–2 nights. (This treatment with BSA prevents interference of the assay by non-specific binding). After removal of the BSA-PBS solution, each well is well-washed with deionized water or a PBS solution, and the antiserum to be tested, diluted with a BSA-PBS solution, is added to each well (100 µl/well). The plate is then allowed to stand at 4° C. overnight. After washing once with deionized water and 6 times with 2M NaCl solution, an appropriate secondary IgG or F (ab')2urease combined product, e.g. in the case of a mouse antiserum an anti-mouse immunoglobulin IgG or F (ab')2urease combined product, [Common Wealth Serum Laboratories, Australia, hereinafter referred to as CSL](X 100; 100 µl/well) is added to each well and the plate is allowed to stand at room temperature for 2 hours. The plate is washed 3 times with deionized water, and a urease substrate solution (CSL) is then poured into each well (100 µl/well). After 10–30 minutes at room temperature, the reaction is discontinued by adding 1% methylthiolate (20 µl per well) and the antibody titre is determined by measuring the optical density at 600 nm.

(b) With whole cells

A Falcon 3072 plate is used for culturing the target cells. After addition of a 0.25% glutaraldehyde-PBS solution, the plate is allowed to stand at room temperature for 1-2 hours. After washing each well with a PBS solution, a 1% BSA-PBS solution (100-200 μl/well) is added to the plate which is then allowed to stand for a further 2 hours. The plate is then well-washed with deionized water or a PBS solution and following the addition of antiserum, diluted with a BSA-PBS solution, (100 μl/well) the antibody titre is determined as in (a).

Antisera from animals immunized with tumour antigens which have previously been treated with normal cell antigens so as to induce immunological tolerance may be compared with antisera from animals not treated with the tolerogen, but identically immunized. Suitable animals for the preparation of antibody-forming cells are tolerogen-treated and immunized animals from which antisera are isolated with high reactivity to tumour tissue fragments, isolated tumour cells or membranes of tumour cells comprising tumour antigens used for immunization, but considerably weaker reactivity than control antisera to normal cell antigens.

3-4 days before the isolation of antibody-forming cells from, for example, spleen, lymph nodes or peripheral blood, it is preferable to give a booster dose of tumour antigens by, for example, abdominal injection. (Suitable dose for mice: tumour tissue fragments or isolated tumour cells, $2-5 \times 10^6$ cells, membrane fragments, 20-400 μg).

The preferred antibody-forming cells are spleen cells which may be isolated as follows.

Removed spleen tissue is cut into small pieces in MEM medium (Nissui Seiyaku K.K., Japan). The cells are loosened by using a pincette and centrifuged (1200 r.p.m./5 min.) to remove supernatant. The remaining material is treated with tris-ammonium chloride buffer solution (pH 7.65) for 1-2 minutes to remove the red cells. The spleen cells obtained by washing the material with MEM medium 3 times may be used for fusion.

Preparation of myeloma cells

Preferred myeloma cells for the purpose of the present invention include various cell lines of mouse origin, for example, myeloma cells originating from 8-azaguanine-resistant BALB/c mice, such as P3-X63-Ag8-U1 (P3-U1) [Current Topics in Microbiology and immunology -1; Euro. J. Immunology, 6, 511-519 (1976)], SP2/0-Ag 14 (SP-2) [Nature, 276, 269-270 (1978)], P3-X63-Ag8.653 (653) [J. Immunology, 123, 1548-1550 (1979)]and P3-X63-Ag8 (X63) [Nature, 256, 495-497 (1975)]. These cell lines may be subcultured using 8-azaguanine medium, prepared by adding 8-azaguanine (15 ug/ml) to RPMI-1640 normal medium containing glutamine (1.5 mM), 2-mercaptoethanol ($5 \times 10^{-5}$M), gentamycin (10 μg/ml) and fetal calf serum (FCS; 10% CSL, Australia)]For 3-4 days prior to carrying out cell fusion, it is preferable to further subculture the chosen myeloma cells using a normal medium.

Cell fusion and selection of hybridoma cells

The preferred method for cell fusion and selection of hybridoma cells is as follows.

The isolated antibody-forming cells and the chosen myeloma cells are well-washed with MEM medium or a PBS solution and mixed together at a ratio of 5-10:1. The mixture is centrifuged (1200 r.p.m./5 min.) to remove supernatant and the precipitated cells are well loosened. To the cells, a solution of polyethylene glycol 1000 (PEG 1000; 2 g), MEM (2 ml) and dimethylsulfoxide (0.7 ml) is added at 37° C. with stirring (0.2-1 ml per $10^8$ antibody-producing cells). MEM medium (1-2 ml) is added to the mixture several times with an interval of 1-2 minutes and then further MEM medium is added to make up the total volume to 50 ml. The mixture is centrifuged (900 r.p.m./5 min.) to remove supernatant and precipitated cells are loosened. After adding a normal medium (100 ml), the cells are suspended using a Mohr pipette.

1 ml of cell suspension is added to each well of a culture plate with 24 wells for culturing at 37° C. for 24 hours, using an incubator containing 5% $CO_2$ gas. 1 ml of HAT medium [prepared by adding to a normal medium hypoxanthine ($10^{-4}$M), thymidine ($1.5 \times 10^{-5}$ M) and aminopterin ($4 \times 10^{-7}$ M)] is then added to each well for culturing for a further 24 hours. Following this, for 2 days, every 24 hours 1 ml of supernatant is removed from each well and replaced by the same amount of new HAT medium. Culturing is continued at 37° C. for 10-14 days in a $CO_2$ incubator. The wells with growing colonies of hybridoma cells are selected. From each of these wells, 1 ml of supernatant is removed and replaced by an equal amount of a HT medium [prepared by adding to a normal medium hypoxanthine ($10-4$M) and thymidine ($1.5 \times 10-5$M)]. This is repeated every 24 hours for 2 days. After culturing for 3-4 days using HT medium, a portion of the supernatant is collected from each culture so as to determine the titre of anti-tumour antibodies by the enzyme immunosorbent assay method hereinbefore described. At the same time, the reactivities of the supernatants with normal cell antigens are also determined by a similar method.

In the case of wells for which negative results are obtained with normal cell antigens, but positive results are obtained with tumour tissue fragments, tumour cells or membrane fragments of tumour cells comprising the tumour antigens used for immunization, Cloning of the hybridoma cells is repeated twice by the limiting dilution method.

From the resultant hybridoma cells, those exhibiting a stable and high antibody titre with respect to tumour-specific antigens are selected.

Preparation of tumour-specific monoclonal antibodies

In order to prepare a desired tumour-specific monoclonal antibody in good yield, hybridoma cells which secrete the monoclonal antibody are preferably administered intraperitoneally to a suitable animal.

For example, a mouse is intraperitoneally injected with 0.5 ml of 2, 6, 10, 14-tetramethyl pentadecan (pristane) and bred for 2 weeks to obtain a pristane-treated mouse of 8-10 weeks. $2-4 \times 10^6$ suitable hybridoma cells, capable of forming a tumour-specific monoclonal antibody, are administered to the mouse by intraperitoneal injection and 10-21 days later the ascites fluid is collected.

Suitable methods for the isolation of monoclonal antibodies of the IgG or IgM class from ascites fluid are as follows:

(a) IgG

The ascites fluid is centrifuged (3000 r.p.m./5 min.) to remove the solid impurities. The supernatant is then subjected twice to salting-out using respectively 50% and 40% ammonium sulphate. After dialysis against a PBS solution (pH 7.2) for 1-2 days, the desired monoclonal antibody is recovered by chromatography using, for example, DEAE Sepharose or Protein A Sepharose (Pharmacia Fine Chemicals AB., Sweden).

(b) IgM

The ascites fluid is centrifuged (3000 r.p.m./5 min.) to remove the solid impurities and the supernatant is then dialyzed against, for example, deionized water or 0.01M phosphate buffer solution (pH 6.0) for 2–4 hours. The precipitates subsequently collected by centrifugation are dissolved in 3–5% sodium chloride solution which is then dialyzed against, for example, 0.85% sodium chloride solution for 1–2 days. The desired monoclonal antibody is finally recovered by chromatography using, for example, DEAE Sepharose or Protein A Sepharose.

The isotypes of the monoclonal antibodies may be investigated by Ouchterlony's method (the double diffusion method) with reference to "Meneki-gaku Jikkenho Nyumon, Seibutsu Kagaku Jikken-ho 15", published by Gakkai Shuppan Centre, Tokyo, p. 74 (1981).

The determination of immunoglobulin protein may be carried out using the Folin's method with reference to the absorbance at 280 nm [1.4 ($OD_{280}$)≃immunoglobulin 1 mg/ml].

It is desirable to investigate the specificities of prepared monoclonal antibodies with reference to their reactivities with a wide range of cells, tissue fragment preparations and membrane fragment preparations derived from both normal and tumour tissues. Reactivities may be determined, for example, using an enzyme-linked immunosorbent assay method, a fluorescence antibody method or an immuno-histological method. Binding to individual antigens, for example, carcinoembryonic antigen (CEA) may also be investigated.

Tumour-specific monoclonal antibodies or antigen-binding fragments of such antibodies may be used for in vitro or in vivo diagnosis of tumours with appropriate tumour-specific antigens (for example, diagnosis of tumours by histological examination and examination of serums) and for treatment of tumours. For the diagnosis of tumours, tumour-specific monoclonal antibodies or antigen-binding fragments of such antibodies may be linked with tracer-labels (e.g. radio labels, fluorescent agents). Tumour-specific monoclonal antibodies and antibody-binding fragments of tumour-specific monoclonal antibodies may also be linked to anti-tumour agents to form products commonly referred to as immunotoxins, which may be used in the treatment of tumours. A further possible use of tumour-specific monoclonal antibodies and antibody-binding fragments of such antibodies is in the purification and characterization of the tumour antigens which they bind. Affinity columns comprising a tumour specific monoclonal antibody or an antigen-binding fragment of such an antibody may, for example, be prepared for this purpose.

The hybridoma cells SLC-1 and ALC-1 described in the following specification have been deposited at The Institute for Fermentation, of 17–85, JusoHonmachi, 2-chome, Yodogawa-ku, Osaka-shi, Japan on 5th March 1985 as IFO 50044 and 50045, respectively.

EXAMPLE 1

(1) Induction of immunological tolerance in mice to antigens of normal lung cells immunization with human lung tumour antigens: preparation of antibody-forming cells.

Newborn BALB/c mice, 24 hours after birth, were administered with CCD-8Lu (ATCC CCL-201) lung cells of human origin ($8 \times 10^5$ cells/mouse) or a broken-cell preparation derived from normal human lung (2–8 mg, calculated as protein/mouse). The administration was effected by intravenous, abdominal and/or subcutaneous injections. 8 weeks later, each mouse was abdominally injected with one member selected from A549 adenocarcinoma cells originating from human lung (ATCC CCL-185) ($2-5 \times 10^6$ cells), a broken cell preparation derived from human lung squamous cell carcinoma (100 μg, calculated as protein) and a broken cell preparation derived from adenocarcinoma of human lung (100 μg, calculated as protein). The chosen immunogen was administered together with aluminium hydroxide gel (2 mg) and pertussis adjuvant ($1 \times 10^9$ cells). After an interval of 1–2 weeks, a higher dose of the same immunogen was abdominally administered to each animal [$2-5 \times 10^6$ A549 adenocarcinoma cells or 100 mg (calculated as protein) of a broken lung tumour cell preparation. 3–4 days after this immunization, blood was collected from the orbital plexus vein of each animal to prepare antiserum. 8-week old BALB/c, not treated so as to induce immunological tolerance with CCD-8Lu cells or a broken CCD-8Lu cell preparation, were identically immunized. Antisera from these mice where compared with the antisera obtained from the tolerogen-treated mice.

The following Tables 1–3 show the reactivities of particular antisera with particular cells, tissue fragments or broken cell preparations. The antibody titres were determined by the enzyme immunosorbent assay method hereinbefore described.

Table 1 indicates the reactivities of two different antisera with CCD-8Lu cells and A549 adenocarcinoma cells. One antiserum was obtained from a mouse immunized with A549 adenocarcinoma cells after treatment with CCD-8Lu cells so as to induce immunological tolerance. The second antiserum was obtained from an identically immunized mouse, not treated with a tolerogen.

TABLE 1

| Tolerogen | Dilution of antiserum (X) | $OD_{600}$ A-549* cells | $OD_{600}$ CCD-8Lu* cells |
|---|---|---|---|
| CCD-8Lu | 1/50 | 0.396 | 0.215 |
| | 1/500 | 0.300 | 0.040 |
| | 1/5000 | 0.087 | 0.000 |
| Untreated | 1/50 | 0.485 | 0.736 |
| | 1/500 | 0.347 | 0.398 |
| | 1/5000 | 0.126 | 0.046 |

*$8 \times 10^9$ cells

Table 2 indicates the reactivities of two different antisera with broken cell preparations derived from normal lung and squamous cell carcinoma of human lung. One antiserum was obtained from a mouse immunised with a broken cell preparation derived from squamous cell carcinoma of human lung after treatment with a broken cell preparation of normal lung so as to induce immunological tolerance. The second antiserum was obtained from an identically immunized mouse, not treated with a tolerogen.

TABLE 2

| Tolerogen | Dilution of antiserum (X) | $OD_{600}$ A | B |
|---|---|---|---|
| Broken cell preparation derived from normal | 1/50 | 0.330 | 0.070 |
| | 1/500 | 0.283 | 0.000 |

TABLE 2-continued

| Tolerogen | Dilution of antiserum (X) | OD$_{600}$ A | B |
|---|---|---|---|
| human lung (100 μg calculated as protein) | | | |
| Untreated | 1/50 | 0.345 | 0.421 |
| | 1/500 | 0.284 | 0.322 |

A = broken cell preparation derived from squamous cell carcinoma of human lung
B = broken cell preparation derived from normal human lung Table 3 indicates the reactivities of two different antisera with broken cell preparations derived from various normal human organs. One antiserum was obtained from a mouse first treated so as to induce immunological tolerance with a broken cell preparation derived from normal human lung and then immunized with a broken lung tumour cell preparation. The second antiserum was obtained from an identically immunized mouse, not treated with a tolerogen.

TABLE 3

| Source of test broken cell preparation | OD$_{600}$ serum of tolerant mouse | serum of untreated mouse |
|---|---|---|
| Heart | 0.027 | 0.213 |
| Spleen | 0.024 | 0.134 |
| Liver | 0.094 | 0.257 |
| Kidney | 0.094 | 0.286 |
| Stomach | 0.033 | 0.195 |
| Large intestine | 0.039 | 0.158 |

When a mouse was treated so as to induce immunological tolerance with a broken cell preparation derived from either a human stomach tumour or a human lung tumour and was then given an immunizing dose of either a broken cell preparation derived from a human stomach tumour or a human lung tumour, it was noted that the resultant mouse antiserum exhibited no reactivity with whole cells, tissue fragments or a broken cell preparation derived from a human stomach tumour or little reactivity compared with an antiserum from a mouse identically immunized, but not treated with a tolerogen. The control antiserum was strongly reactive with tissue fragments, and isolated whole cells or broken cells derived from a human stomach tumour.

Mice treated with a tolerogen from which antisera were obtained which exhibited no or little reactivity compared with control antisera with normal human cell antigens, but which exhibited strong reactivity with human squamous cell carcinoma and/or human lung adenocarcinoma were used for the preparation of spleen cells. The spleen of each selected animal was collected 3-4 days after the final immunization. cl (2) Preparation of mouse myeloma cells:

Myeloma cells of the cell line P3-U1, originating from a 8-azaguanine-resistant mouse, were cultured using a normal medium. The resultant cells (more than 2×10$^7$ cells) were used for hybridization. (3) Preparation of hybridoma cells:

The spleen cells obtained by step (1) and the myeloma cells obtained by step (2) were mixed together at a ratio of 5:1. Cell fusion was effected in the manner hereinbefore described. The fused cells were cultured at 37° C. for 14 days using a HAT medium in a 5% CO$_2$ atmosphere. Growing hybridoma cells were selected and further cultured as hereinbefore described. The anti-human tumour activities of the culture supernatants were determined. At the same time, reactivities of the supernatants with normal cell antigens were determined. By means of the limiting dilution method, hybridoma cell clones were obtained, which produce monoclonal antibodies capable of binding to human lung squamous cell carcinoma and/or human lung adenocarcinoma, but not normal tissues (SLC 1-6 and ALC 1-4).

(4) Purification of monoclonal antibodies:

The hybridoma cells obtained by step (3) were abdominally administered to pristane-treated mice (BALB/c; female; 8 weeks after birth) in an amount of 4×10$^6$ cells per animal. 10-21 days later, ascities fluid was collected from the mice and centrifuged (3000 r.p.m./5 min.) to remove solid impurities. The remaining solution was dialyzed against deionized water or a 0.01M PBS solution (pH 6.5) for 2 hours. The residual solution was centrifuged (10,000 r.p.m./15 min.) to remove supernatant. The remaining material was dissolved in a 3% sodium chloride solution and was dialyzed against a 0.85% sodium chloride solution. The residual solution was used as a partially purified monoclonal antibody (IgM class) solution. (5) The specificity of the monoclonal antibodies produced by hybridoma cells of the cell lines SLC 1-6 and ALC 1-4

The IgM class monoclonal antibodies of hybridoma cells of the cell lines SLC 1-6 and ALC 1-4, were tested for binding with a variety of tissues and cells and also carcinoembryomic antigen, using a conventional fluoroescence method. (See e.g. Immunofluorescence Technology in selected Theoretical and Clinical Aspects, ed. G. Wick, K. N. Trail and K. Schauenstein, Elsevier Biomedical Press.) The results are summarized in Table 4.

TABLE 4

Characteristics of anti-human lung cancer monoclonal antibodies

A: broken cell preparation derived from squamous cell carcinoma of human lung
B: broken cell preparation from adenocarcinoma of human lung
CEA: carcinoembryonic antigen
Site: site of antigen
S: membrane
I: interior of the cell
Class: class of antibody

| Antibody | Immunogen | Tissue tested | | | | Cells tested | | | | | CEA | Class | Site |
|---|---|---|---|---|---|---|---|---|---|---|---|---|---|
| | | 1 | 2 | 3 | 4 | 1 | 2 | 3 | 4 | 5 | | | |
| SLC-1 | A | ++ | − | − | − | + | − | − | − | − | − | IgM | S |
| SLC-2 | A | ++ | + | − | − | + | ± | − | − | − | − | IgM | S |
| SLC-3 | A | ++ | ++ | − | − | + | ++ | ++ | ++ | − | − | IgM | S |
| SLC-4 | A | ++ | ++ | − | − | + | ++ | ++ | ++ | − | − | IgM | I |
| SLC-5 | A | ++ | ++ | − | − | + | ++ | ++ | ++ | − | − | IgM | I |

TABLE 4-continued

Characteristics of anti-human lung cancer monoclonal antibodies

A: broken cell preparation derived from squamous cell carcinoma of human lung
B: broken cell preparation from adenocarcinoma of human lung
CEA: carcinoembryonic antigen
Site: site of antigen
S: membrane
I: interior of the cell
Class: class of antibody

| Anti-body | Immuno-gen | Tissue tested | | | | Cells tested | | | | | CEA | Class | Site |
|---|---|---|---|---|---|---|---|---|---|---|---|---|---|
| | | 1 | 2 | 3 | 4 | 1 | 2 | 3 | 4 | 5 | | | |
| SLC-6 | A | ++ | + | − | − | + | ++ | ++ | ++ | − | − | IgM | S |
| ALC-1 | B | − | ++ | − | − | − | ++ | − | − | − | − | IgM | S |
| ALC-2 | B | ++ | ++ | − | − | + | ++ | − | − | − | − | IgM | S |
| ALC-3 | B | ++ | ++ | − | − | + | + | + | + | − | − | IgM | S |
| ALC-4 | B | ++ | ++ | − | − | + | ++ | + | + | − | − | IgM | I |

Tissues
1 squamous cell carcinoma (lung);
2 adenocarcinoma (lung);
3 normal lung;
4 normal tissues other than lung
Cells
1 squamous cell carcinoma (lung);
2 adenocarcinoma (lung);
3 lung (fetal),
4 cancers other than lung cancer, including leukemia, stomach cancer, large intestine cancer, uterine cancer, trophoblastic neoplasia, neuroblastoma, melanoma and myeloma;
5 normal lung.

From Table 4, it is apparent that these monoclonal antibodies may be used for diagnosis and treatment of tumours, since they are not reactive with human normal cells and tissues, but specifically reactive with tumour cells and tissues. In particular, SLC-2 and ALC-2 are especially useful for diagnosis and treatment of lung cancer, and SLC-1 and ALC-1 are respectively useful for diagnosis and treatment of lung squamous cell carcinoma and adenocarcinoma.

Example 2

To obtain hybridoma cell lines which produce monoclonal antibodies capable of binding to human stomach squamous cell carcinoma and/or human stomach adenocarcinoma, but not normal human tissues, a similar procedure to that described in Example 1 was carried out. A broken cell preparation derived from human stomach was administered to mice so as to induce immunological tolerance and the same mice were then immunized with a broken cell preparation derived from either squamous cell carcinoma of human stomach or human adenocarcinoma of human stomach. The IgM class monoclonal antibodies of 7 hybridoma cell lines which were selected were tested for binding with a variety of tissues and cells and also carcinoembryonic antigen as in Example 1. The results are summarized in Table 5.

TABLE 5

Characteristics of anti-human stomach cancer monoclonal antibodies

A: broken cell preparation of squamous cell carcinoma of human stomach
B: broken cell preparation of adenocarcinoma of human stomach
CEA: carcinoembryonic antigen,
Site: site of antigen,
S: membrane
I: interior of the cell
Class: class of antibody

| Anti-body | Immuno-gen | Tissue tested | | | | | Cells tested | | | | CEA | Class | Site |
|---|---|---|---|---|---|---|---|---|---|---|---|---|---|
| | | 1 | 2 | 3 | 4 | 5 | 1 | 2 | 3 | 4 | | | |
| SMC-1 | A | ++ | − | − | − | − | ++ | − | − | − | − | IgM | S |
| SMC-2 | A | ++ | ++ | − | − | − | ++ | + | − | − | − | IgM | S |
| SMC-3 | A | ++ | ++ | − | − | + | ++ | ++ | ++ | − | − | IgM | S |
| AMC-1 | B | − | ++ | − | − | − | − | + | − | − | − | IgM | S |
| AMC-2 | B | + | + | − | − | − | + | + | − | − | − | IgM | S |
| AMC-3 | B | + | ++ | − | − | + | + | ++ | + | − | − | IgM | S |

TABLE 5-continued

Characteristics of anti-human
stomach cancer monoclonal antibodies

A: broken cell preparation of squamous cell carcinoma
   of human stomach
B: broken cell preparation of adenocarcinoma
   of human stomach
CEA: carcinoembryonic antigen,
Site: site of antigen,
S: membrane
I: interior of the cell
Class: class of antibody

| Anti-body | Immuno-gen | Tissue tested | | | | | Cells tested | | | | CEA | Class | Site |
|---|---|---|---|---|---|---|---|---|---|---|---|---|---|
| | | 1 | 2 | 3 | 4 | 5 | 1 | 2 | 3 | 4 | | | |
| AMC-4 | B | + | ++ | − | − | + | + | + | ++ | − | − | IgM | I |

Tissues
1 squamous cell carcinoma (human stomach)
2 adenocarcinoma (human stomach)
3 normal stomach
4 normal tissues other than stomach
5 stomach (fetal)
Cells
1 squamous cell carcinoma (stomach)
2 adenocarcinoma (stomach)
3 cancers other than stomach cancer, including leukemia, stomach cancer, large intestine cancer, uterine cancer, trophoblastic neoplasia, neuroblastoma, melanoma and myeloma,
4 normal stomach.

We claim:

1. In the process for producing mouse monoclonal antibodies which bind to tumer-associated antigens of human carcinomas selected from the group consisting of lung and stomach carcinomas by immunizing neonatal mice to the antigens from said carcinomas, the improvement which comprises the step of tolerizing said neonatal mice to normal adult cell antigens by the immunization of said mice to normal human adult cell antigens prior to the conventional immunizing of said mice with said cancer antigens to form said mouse monoclonal antibodies.

2. The process as claimed in claim 1 wherein the animal immunized is first treated so as to induce immunological tolerance with (a) one member selected from isolated cells, broken cells, tissue fragments and membrane fragments originating from a normal organ of the same type as that from which the tumour antigens chosen for subsequent immunization are derived, or (b) one member selected from isolated cells, broken cells, tissue fragments and membrane figments originating from various organs comprising appropriate antigens.

3. The process as claimed in claim 1 wherein tumour tissue fragments, isolated tumour cells, broken tumour cells or membrane fragments of tumour cells are used for immunization.

4. A process as claimed in claim 1 wherein a neonatal mouse is first treated so as to induce immunological tolerance with whole or broken cells originating from normal human lung and is then immunized with whole or broken cells originating from a squamous cell carcinoma of human lung or an adenocarcinoma of human lung.

5. A process as claimed in claim 1 wherein a neonatal mouse is first treated so as to induce immunological tolerance with whole or broken cells originating from normal human stomach and is then immunized with whole or broken cells originating from a squamous cell carcinoma of human stomach or an adenocarcinoma of human stomach.

6. Murine monoclonal antibodies which bind to an antigen specific to human lung squamous carcinoma derived from a hybridoma cell SLC-1 (IFO - 50044).

7. Murine monoclonal antibodies which bind to an antigen specific to human lung adenocarcinoma derived from a hybridoma cell ALC-1 (IFO - 50045).

* * * * *